United States Patent [19]
Bayless et al.

[11] Patent Number: 5,944,696
[45] Date of Patent: Aug. 31, 1999

[54] SWIVEL CLIP MEDICAL TUBE HOLDER

[76] Inventors: William Brian Bayless, 10132 Beverly Dr., Huntington Beach, Calif. 92646; Harry Nicholas Herbert, 33771 Killarney La., San Juan Capistrano, Calif. 92675

[21] Appl. No.: 08/657,379

[22] Filed: Jun. 3, 1996

[51] Int. Cl.⁶ .................................................. A61M 5/32
[52] U.S. Cl. .................. 604/174; 604/180; 128/DIG. 26
[58] Field of Search .................... 604/174, 175, 604/177, 180; 128/DIG. 26

[56] References Cited

U.S. PATENT DOCUMENTS

| | | | |
|---|---|---|---|
| 2,590,006 | 3/1952 | Gordon | 604/180 |
| 3,338,538 | 8/1967 | Roche | 128/DIG. 26 X |
| 3,782,388 | 1/1974 | Page | 128/DIG. 26 X |
| 4,170,995 | 10/1979 | Levine | 604/180 |
| 4,634,425 | 1/1987 | Meer | 128/DIG. 26 X |
| 4,660,555 | 4/1987 | Payton | 128/207.18 |
| 4,666,433 | 5/1987 | Parks | 128/DIG. 26 X |
| 4,717,385 | 1/1988 | Cameron et al. | 128/DIG. 26 X |
| 5,188,609 | 2/1993 | Bayless | 604/180 |
| 5,382,242 | 1/1995 | Horton et al. | 128/DIG. 26 X |

*Primary Examiner*—Sam Rimell
*Assistant Examiner*—Luke Yeh
*Attorney, Agent, or Firm*—G. Donald Weber, Jr.

[57] ABSTRACT

A holder for securely, but removably, attaching a medical tube to the body of a patient. The holder comprises a clip releasably connectable to the medical tube, a base for supporting the clip and a connecting component for connecting the clip to the base. An adhesive pad can be associated with the base to secure the holder to the patient.

12 Claims, 1 Drawing Sheet

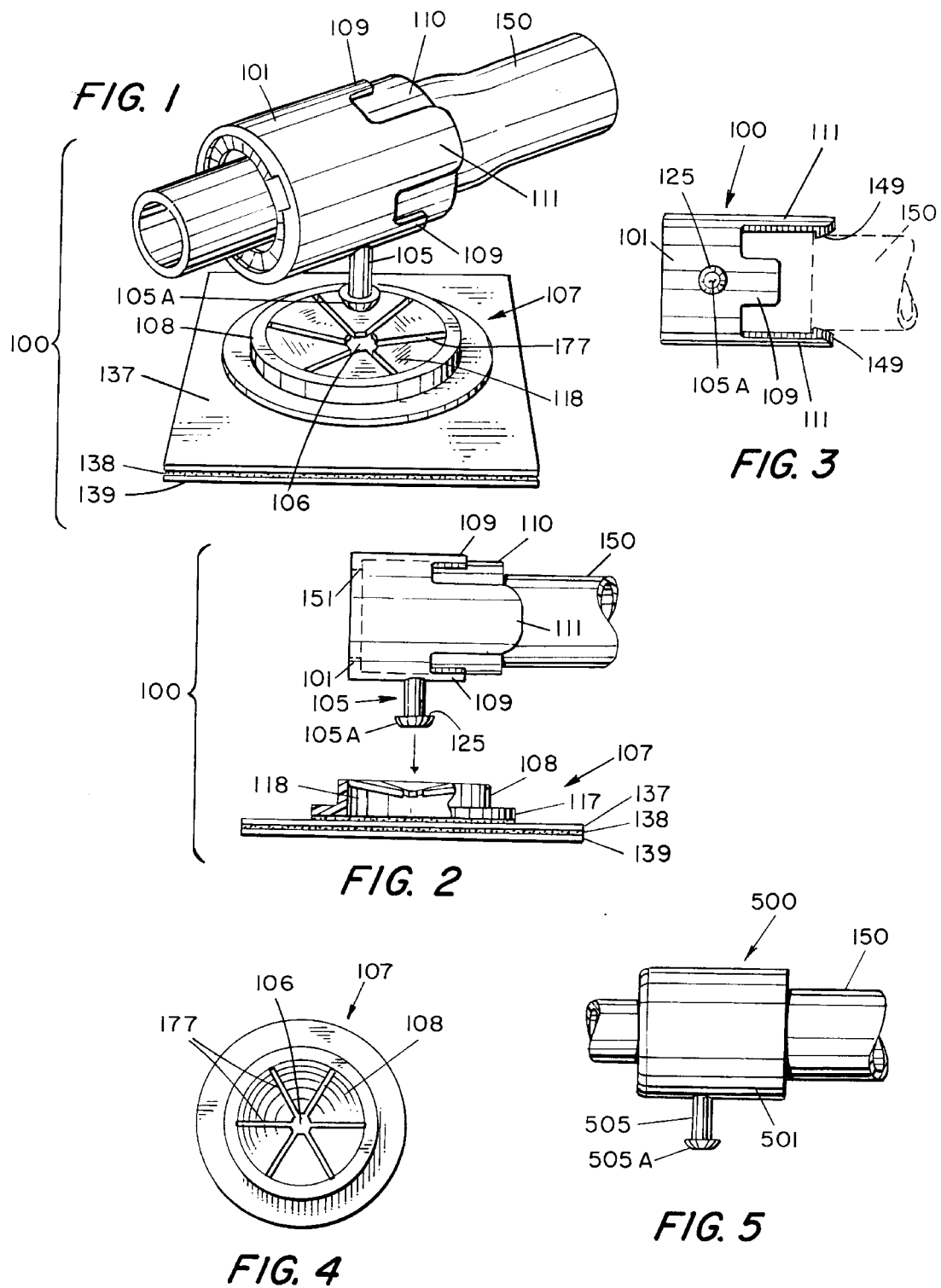

SWIVEL CLIP MEDICAL TUBE HOLDER

BACKGROUND OF THE INVENTION

1. Field of the Invention

This invention relates to a holder for a medical tube, in general, and to a holder for attaching a medical tube to the body of a patient in order to enhance patient comfort and safety during medical procedures, in particular.

2. Prior Art

Many medical and surgical procedures require drainage and/or injection tubes to be applied to a patient. These tubes include Foley catheters, bladder catheters, nose tubes, drainage tubes, intravenous tubes, cannulas, and the like. In use, such tubes extend from the body of the patient to a fluid source or drainage receptacle. It is frequently necessary to provide support for the tubes along the length thereof. This support is intended to prevent dislodging of the tube or fittings from the patient and/or the source/drain units.

Typically, in the past, the medical tube has been taped directly to the body of the patient. Of course, the tube can be attached to splints or other devices which are also mounted on the body of the patient. As a result in these prior types of mountings, the connection and the mounting is extremely unstable and/or quite inflexible. This unstable, inflexible connection becomes more uncomfortable the longer it remains in place. Thus, it is a frequent source of complaints by the patient. Moreover, the patient frequently moves and, deliberately or inadvertently, causes the medical tube or fitting to become dislodged. Obviously, when the tube or fitting is dislodged, leakage or drainage can occur. Such leakage or drainage can be frequently hazardous to the patient. In addition, it is wasteful of the materials which are to be provided to the patient. On the other hand, it is frequently unsanitary and, at least, unpleasant if the bodily fluids are discharged into the wrong location. The medical problems associated therewith such as infection and the like are clear.

Moreover, the utilization of tape directly on the body of the patient frequently causes rashes, inflammation and/or bed sores which are unpleasant to the patient and potential sources of infection or the like. The removal of this tape is another source of discomfort to the patient.

A more suitable method of mounting the tubing to the patient so that the disadvantages are overcome is clearly necessary and desirable.

PRIOR ART STATEMENT

The results of a preliminary patentability search are listed herewith. The patents uncovered during the search are listed in descending numerical order without any specific ranking thereof.

U.S. Pat. No. 5,188,609; SWIVEL CLIP MEDICAL TUBE HOUSING; B. Bayless et al. A holder comprising a clip releasably connectable to a medical tube, a support base and a connecting component for connecting the clip to the base.

U.S. Pat. No. 4,915,694; ANTIMICROBIAL WOUND DRESSING AND SKIN FIXATOR FOR PERCUTANEOUS CONDUITS; R. Yamamoto et al. This patent is directed to an antimicrobial catheter shield which comprises an elastomeric catheter collar and a planar porous elastomeric peripheral flange with an absorbent patch which includes an antimicrobial agent attached to the flange opposite the collar.

U.S. Pat. No. 4,856,504; ANTIMICROBIAL WOUND DRESSING AND SKIN FIXATOR FOR ORTHOPEDIC PINS; R. Yamamoto et al. This patent is directed to an antimicrobial orthopedic pin percutaneous protection kit comprising the combination of a shield, a pad and a patch.

U.S. Pat. No. 4,660,555; OXYGEN DELIVERY AND ADMINISTRATION SYSTEM; H. Payton. This patent is directed to a system for supplying supplemental oxygen to a patient through a nose piece and an oxygen-tube holder wherein the tube holder is adapted to be mounted on an EKG electrode-type patch on a cheek prominence of the patient.

U.S. Pat. No. 4,360,025; CATHETER RETAINER; J. V. Edwards. This patent is directed to a catheter retainer which includes a plastic member having a central hole defined by a pair of resilient catheter-gripping jaws and a resilient catch member for holding the jaws in the relatively closed position.

U.S. Pat. No. 4,057,066; CATHETER HOLDER FOR SECURING A URETHRAL CATHETER TO A PATIENT; H. E. Taylor. This patent is directed to a holder for securing a urethral catheter to a patient. It includes an anchoring strip with a pressuresensitive adhesive layer covered by a peel-off cover sheet and a cord which passes through a pair of adjacent openings in the anchoring strip.

U.S. Pat. No. 4,025,015; DETACHABLE ARTICLE-MOUNTING DEVICE; E. S. Kolic. This patent is directed to a mounting device which includes first and second adapters having separable plug-and-socket engagement to each other. One of the adapters includes a means for mounting the same to a relatively thick surface by adhesive means.

U.S. Pat. No. 3,782,388; MEDICAL TUBE HOLDER; S. J. Page. This patent is directed to an article for attaching a medical tube to the body of a patient and comprises a clip releasably connectable to the medical tube, a pad having adhesive on one side thereof for adherence to the body of the patient and a flexible, stretchable band connected between the clip and the pad.

U.S. Pat. No. 3,702,612; CATHETER SUPPORT; R. M. Schlesinger. This patent is directed to a catheter support which has a yoke attached to a base plate by a resilient beam capable of accommodating limited motion of the catheter without pulling the catheter from the patient. The base plate is adhesively backed for placement on the patient's body surface.

U.S. Pat. No. 3,146,778; CATHETER SUPPORT; H. A. Krawiec. This patent is directed to a catheter support which includes a pair of elements, one for holding the catheter and the other for securing to the body of the patient. The two elements are snapped together when support of the catheter is needed.

SUMMARY OF THE INSTANT INVENTION

This invention provides a holder for mounting a medical tube to the body of a patient. The holder prevents the easy dislodgment of all types of medical tubes such as IV tubes, catheters and the like from a patient while permitting increased comfort to the patient. The present invention eliminates the unstable, inflexible attachment technique of the prior art and replaces same with a holder which is able to swivel so as to provide a substantial degree of freedom of movement between the medical tube and the body of the patient. By being able to swivel and pivot, the holder puts no undue pressure or stress on the skin site. This arrangement inhibits breakdown or trauma to the skin site.

The tube holder of the instant invention includes a clip in the form of a cylinder or other suitable configuration which can be readily locked or unlocked to a tube end. A base for mounting on (or adjacent to) the patient's body is provided. The base can be adhered to the skin of the patient or to the patient's bedding through a suitable adhesive. The clip includes a stem which is detachably joined to the base in a manner that permits the clip to swivel in relation to the base.

BRIEF DESCRIPTION OF THE DRAWINGS

FIG. 1 is a perspective view of one embodiment of the holder of the instant invention.

FIG. 2 is an exploded view of the holder of the instant invention shown in FIG. 1.

FIG. 3 is a plan view of the bottom of the clip portion of the holder of the instant invention shown in FIG. 2 rotated by 90°.

FIG. 4 is a plan view of the base portion of the holder of the instant invention shown in FIG. 2.

FIG. 5 is a side, elevation view of the clip portion of another embodiment of the instant invention.

DESCRIPTION OF THE PREFERRED EMBODIMENT

Referring now to FIG. 1, there is shown a perspective view of one embodiment of the tube holder 100 of the instant invention. The holder 100 includes a tube-retaining clip 101, an interlocking unit 105 and a base 107. In a preferred embodiment, a suitable adhesive patch 108 can be provided at the underside of base 107 for securing the holder 100 to the body of a patient (not shown).

More particularly, the clip 101 includes a generally cup-shaped retainer 101 formed of a suitable material such as nylon or the like. The retainer includes at least one support end 109 for supporting the end 110 of a section of tubing 150 such as a catheter or the like. In the preferred embodiment, the retainer also includes at least one grip tab 111 which will securely engage the end 110 of the tubing but will easily separate therefrom to release the tubing 150. The tab (or tabs) 111 should be able to endure several flexing operations without breaking or losing resilience. The grip tab 111 of clip 101 includes an in-facing ledge (see FIG. 2) at or near the ends thereof. The ledges are utilized to provide an interlocking relationship with the end 110 of the tubing 150. The ledges can take any shape or configuration desired. However, the ledges provide a secure interlocking relationship between the tabs of clip 101 and the tubing end 110 which is shown as a ring or hollow cap secured at the end of tubing 150. It is understood, of course, that the number of tabs can be varied. That is, a single tab or a plurality of tabs is contemplated.

The retainer portion of clip 101 is configured to receive appropriate tubes 150 or the like. Depending upon the type of tube 150 to be utilized, different dimension clips 101 can be utilized so that the tube 150 can be securely retained within the clip 101 without producing any constriction in the tube.

An interlocking unit 105 extends outwardly from the cup-shaped clip 101 and includes an enlarged end 105A which is adapted to engage the base 107 by passing through the opening 106 therein.

The base 107 includes the raised central portion thereof which defines a dome-like structure 108 which receives the end of interlocking unit 105. An aperture 106 is formed in the upper surface of the dome 108 in the base 107. The end 105A of connector 105 passes through the aperture 106 into the cavity 118 under dome 108. The end 105A of connector 105 is appropriately sized so that it engages and slidably interlocks with the undersurface of dome 108 in base 107.

In a preferred embodiment, the upper surface of base 107 may include a plurality of radial slits 177. Thus, the upper surface is sufficiently flexible to permit the end 105A of connector 105 to pass through aperture 106, but sufficiently rigid to retain the end 105A of connector 105 therein.

In either case, connector 105 is free to rotate about the axis thereof which passes through the aperture 106 of housing 107. Thus, the connector 105 can rotate through 360°. The clip 101, which is joined to connector 105 can, therefore, rotate through 360°, as well.

In one embodiment, a base support 137, such as adhesive tape or the like, is fastened to the undersurface of base 107. A release liner 139 is selectively removed whereupon the base support 137 can be attached to the patient (or adjacent thereto) by adhesive layer 138. Alternatively, the adhesive layer 138 can be provided directly on the undersurface of base 107, per se. Thus, the support device 100 can be mounted securely to a bed or to a patient. In either case, the adhesive layer 138 is conventional and may include any suitable adhesive material 109 such as adhesive tape, a gel adhesive, or the like. A peelable liner 137 can be used with the adhesive layer.

Referring now to FIG. 2, there is shown an exploded, side elevation view of the holder 100. The generally cup-shaped clip 101 is shown engaging the end cap 110 of tubing 150. As shown, the clip 101 has a generally cylindrical configuration. The clip includes one or more tabs which secure the tubing while remaining somewhat flexible and pliant. That is, tabs 111 of the clip include ends which extend inwardly toward each other to form a pair of grasping ledges (see FIG. 3) which will engage the end 110 of a tubing 150. The tabs 109 assist in holding the clip 101 to the tubing 150 with or without the ends 102. The other end of the cup-shaped clip 101 includes an opening 151 for interconnecting the tubing 150 to any other tubing or similar device.

The clip 101 is, as noted, fabricated of nylon (or other suitable medical grade material) and configured to have a degree of hysteresis so that the tabs 111 tend to return to the original position whereby the interlocking between the clip 101 and tubing 150 is achieved.

The base 107 is shown to have a relatively flat lower surface 117 with an upraised, dome-like center portion 108 which produces a cavity or chamber 118 at the center portion of the base 107. The chamber 118 is provided to receive the end 105A of the connector 105. The connector 105 is a relatively thin peg-like member which includes end 105A which has a flange 125 (or ledge) at the end thereof. The flange 125 extends outwardly from the sides of connector end 105A and engages the underside of the upraised center portion 108 of base 107. The aperture 106 (see FIG. 4) passes through the base 107, typically, at the center of the dome 108. The connector end 105A passes through the aperture 106 and is free to rotate through 360° relative to the base 107.

Typically, connector 105 has end 105A thereof which is passed through aperture 106 in dome 108. This arrangement can be enhanced by applying a bevel or chamfer to the end 105A of connector 105. However, the upper surface of the flanges 125 engages the undersurface of the dome 108 in the base 107 so that the connector 105 does not inadvertently pull out through the aperture 106. Moreover, as seen, the connector 105 is free to rotate through 360° thereby carrying with it the clip 101 which also rotates through 360°.

Referring now to FIG. 3, there is shown a bottom view of the holder 100 of the instant invention wherein the tubing 150 and other parts are shown in phantom outline. In this view, clip 101 of the holder 100 is rotated 90° relative to FIG. 2. In particular, there is shown a view of the ends of tabs 111 of the clip 101 as related to tubing 150 and 110. The clip 101 includes the tabs 109 and 111. In particular, the tabs 111 are shown to be relatively thin with ledges 149 extending inwardly from the inner surface thereof.

The ends 102 of the clip 101 are generally rectiliner in shape. Again, the end configurations can be of any desired shape or omitted altogether, as desired.

Likewise, the connector 105 which extends from clip 101 has a generally cylindrical configuration and includes the end 105A which is somewhat large in diameter. This is not a requirement of the device. However, it provides a somewhat greater degree of flexibility and movement of the clip 101 as well as ensuring retention of the clip 101 by the base 107.

The connector end 105A includes the flanges 125 shown in FIG. 2. The flange, as noted above, engages the undersurface of base 107 adjacent to aperture 106 so that the expanded end of connector 105 will not pass through the opening 106.

Referring now to FIG. 4, there is shown a plan view of base 107. The base 107 includes aperture 106 through which connector end 105A is inserted. If necessary, base 107 may include one or more cuts 177 extending radially outwardly from aperture 106 to provide flexibility for receiving connector 105. The clip 101 is free to rotate and pivot as described supra. The neck 105 permits a degree of freedom of movement even though the connector end 105A knob 505 remains trapped in the base 107.

Referring now to FIG. 5, there is shown another embodiment of the instant invention. In this embodiment, holder 500 is quite similar to holder 100 shown in FIG. 1. However, in this case the clip 501 is formed directly on the end of tubing 150. In this embodiment, the connector comprises a spherical knob 505 formed on a short neck 505 which extends from clip 501. The knob 505 and the connector 105 (shown and described supra) are substantially identical in function.

In operation, holder 100 is used for mounting a medical tube 150 on or adjacent to the body of a patient (not shown). Tube 150 is, typically, draped over the patient and mounted thereto. To use holder 100, the protective sheet 139 is removed from the adhesive layer 138 on base 107 or base support 137. The base 107 or base support 137 is attached adjacent to the body of the patient, as desired. Clip 101 is attached to tube 150. The clip 101 will securely grip tube 150, thereby restricting movement thereof. Clip 101 is then attached to the base 107 by inserting the connector 105 through the aperture 106.

The resultant attachment of tube 150 to the body of the patient greatly enhances patient comfort and safety during a variety of medical procedures. With holder 100, the rigid, inflexible attachment techniques of the prior art are eliminated and replaced by a holder having built-in, multi-direction motion capability which permits relative movement between medical tube 150 and the body of the patient. As a result, slight patient movement is permitted without discomfort and skin breakdown or trauma. Moreover, the possibility of tube dislodgement is significantly reduced. Holder 100 is simple and may be manufactured and sold inexpensively so that it may be used only once and thereafter discarded.

Thus, there is shown and described a unique design and concept of a swivel clip medical tube holder. The particular configuration shown and described herein relates to a holder for IV tubing or the like. In a preferred embodiment, the holder is formed of a suitable plastic material such as nylon, polyethylene, Delrin or the like. However, any appropriate material can be used. Moreover, the holder can be formed in a one-piece or in a multi-piece configuration. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

We claim:

1. A holder for tubing comprising, retainer means for snugly and securely retaining one end of a tubing therein without constricting the tubing, said retainer means having a cylindrical configuration which is adapted to completely surround the tubing, base means, and connector means formed on said retainer means for securely connecting said retainer means to said base means while permitting said retainer means to freely move relative to said base means while said retainer means snugly and securely retains the one end of the tubing without constricting the tubing, said connector means includes a knob which extends from said retainer means, and neck means connected between said knob and said retainer means, said base means includes a raised central portion thereof which defines a dome-like structure with a cavity thereunder for receiving and engaging said connector means, said dome-like structure includes a plurality of slots therein for passing at least said knob of said connector means into said cavity.

2. The holder recited in claim 1 wherein, said retainer means includes a pair of spaced apart arms for receiving the tubing therebetween and extending longitudinally along the tubing.

3. The holder recited in claim 2 including, interlocking means on at least one of said arms adapted to encompass and engage said tubing.

4. The holder recited in claim 1 including, adhesive means on the undersurface of said base means for adhering said base means to a surface.

5. The holder recited in claim 1 including, at least one gripping means on the inner surface of said retainer means to engage the one end of the tubing.

6. The holder recited in claim 5 wherein, said gripping means comprises a projection extending inwardly from the inner surface of said retainer means to engage the one end of the tubing.

7. The holder recited in claim 1 wherein, said retainer means and said connector means are integrally formed.

8. The holder recited in claim 4 wherein, said adhesive means includes a base support means which is adhered to said base means.

9. The holder recited in claim 1 wherein, said retainer means includes at least one tab for engaging said tubing retained in said retainer means.

10. A tubing holder comprising, cup-shaped retainer means for snugly and securely retaining one end of a flexible tube therein without constricting the tube, said retainer means having an opening therethrough which receives the one end of the flexible tube such that said retainer means completely surrounds the one end of the flexible tube, base means having a plurality of slots, and connector means formed on the side of said retainer means for securely connecting said retainer means to said base means while permitting said retainer means to freely move relative to said base means.

11. The holder recited in claim 10 wherein, said retainer means includes a pair of spaced apart arms extending therefrom for securely receiving the one end of the flexible tube therebetween.

12. The holder recited in claim 11 including, interlocking means on at least one of said arms adapted to encompass and engage the one end of the flexible tube.

* * * * *